US008228505B2

(12) United States Patent
Narahara et al.

(10) Patent No.: US 8,228,505 B2
(45) Date of Patent: Jul. 24, 2012

(54) APPARATUS AND METHOD FOR DETECTING TARGET SUBSTANCE, OR DEVICE USED FOR THESE APPARATUS AND METHOD

(75) Inventors: Masatoshi Narahara, Hitachinaka (JP); Satoshi Takahashi, Hitachinaka (JP); Toshiro Saito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 271 days.

(21) Appl. No.: 12/233,184

(22) Filed: Sep. 18, 2008

(65) Prior Publication Data
US 2009/0079988 A1  Mar. 26, 2009

(30) Foreign Application Priority Data
Sep. 21, 2007  (JP) ................. 2007-244625

(51) Int. Cl.
*G01N 21/55* (2006.01)
(52) U.S. Cl. ...................................... 356/445
(58) Field of Classification Search .......... 356/432, 356/441, 445–448; 385/12, 17, 30; 372/26, 372/28, 32, 38.01–38.02, 45.01–46.016, 372/96; 422/82.05, 82.11
See application file for complete search history.

(56) References Cited

U.S. PATENT DOCUMENTS

| 6,214,560 | B1 * | 4/2001 | Yguerabide et al. ........... 506/3 |
| 6,917,726 | B2 | 7/2005 | Levene et al. |
| 6,989,277 | B2 * | 1/2006 | Yang et al. .................. 436/518 |
| 7,622,027 | B1 * | 11/2009 | Cunningham ............... 204/612 |
| 2003/0132392 | A1 * | 7/2003 | Kuroda et al. .............. 250/397 |
| 2004/0132172 | A1 | 7/2004 | Cunningham et al. |
| 2006/0238767 | A1 * | 10/2006 | Chen et al. ................. 356/445 |
| 2007/0090411 | A1 * | 4/2007 | Naya et al. ................. 257/226 |
| 2007/0263221 | A1 * | 11/2007 | Naya et al. ................. 356/432 |

FOREIGN PATENT DOCUMENTS

EP  1 674 855 A  6/2006

OTHER PUBLICATIONS

Braslavsky, I., et al., "Sequence information can be obtained from single DNA molecules," PNAS, www.pnas.org/cgi/doi/10.1073/pnas.0230489100, Apr. 1, 2003, p. 3960-3964, vol. 100, No. 7.

(Continued)

*Primary Examiner* — Tarifur Chowdhury
*Assistant Examiner* — Michael P LaPage
(74) *Attorney, Agent, or Firm* — McDermott Will & Emery LLP

(57) ABSTRACT

An object of the present invention relates to detecting a target substance with high contrast. The invention relates to analysis of a target substance using a light-transmitting substrate and a metal for inducing plasmon resonance, and further using a low refractive index layer with an opening portion, which forms an interface with the substrate, and which has a lower refractive index than the substrate. Light emitted from a substrate side is totally reflected at the interface to irradiate the metal arranged in the opening portion with evanescent light. Light generated from the target substance by plasmon resonance of the evanescent light is detected. According to the invention, the radiation of evanescent light to a material other than the target substance can be reduced, and thereby light emission from the martial other than the target substance, e.g., a molecule floating around the target substance, can be reduced.

10 Claims, 7 Drawing Sheets

OTHER PUBLICATIONS

Malicka, J., et al., "DNA Hybridization Using Surface Plasmon-Coupled Emission," Analytical Chemistry, Dec. 1, 2003, p. 6629-6633, vol. 75, No. 23, American Chemical Society.

Ruparel, H., et al., "Design and synthesis of a 3'-O-allyl photocleavable fluorescent nucleotide as a reversible terminator for DNA sequencing by synthesis," PNAS, www.pnas.org/cgi/doi/10.1073/pnas.0501962102, Apr. 26, 2005, p. 5932-5937, vol. 102, No. 17, The National Academy of Sciences of the USA.

Korlach, J., et al., "Selective aluminum passivation for targeted immobilization of single DNA polymerase molecules in zero-mode waveguide nanostructures," PNAS, www.pnas.org/cgi/doi/10.1073/pnas.0710982105, Jan. 29, 2008, p. 1176-1181, vol. 105, No. 4, The National Academy of Sciences of the USA.

European Search Report issued in European Patent Application No. EP 08016588.9-2204, dated Jan. 20, 2009.

Nishikawa, T. et al., "A nanobiosensor fabricated by nanoimprinting technology," Solid-State Sensors, Actuators and Microsystems Conference, 2007, pp. 2299-2302, XP022476183.

Nishikawa, T. et al., "Development of new localized surface Plasmon resonance sensor with nanoimprinting technique" Nano/Micro Engineered and Molecular Systems, 2006, pp. 262-265, XP002476184.

* cited by examiner

APPARATUS AND METHOD FOR DETECTING TARGET SUBSTANCE, OR DEVICE USED FOR THESE APPARATUS AND METHOD

BACKGROUND OF THE INVENTION

1. Field of the Invention

The present invention relates to a technology for detecting a target substance by using evanescent light. Specifically, the present invention relates to, for example, a technology for fluorescence detection of a large number of DNAs, proteins, or the like by using evanescent light.

2. Description of the Related Art

As a means for detecting a target substance, such as DNA or protein, there is a widely-used method including: attaching a fluorescent label to a target substance; irradiating the labeled target substance with predetermined excitation light, such as a laser; and detecting the fluorescence emitted from the labeled target substance. The methods for detecting fluorescence with high contrast include a detection method using, as excitation light, evanescent light generated by total internal reflection. In this method, a labeled substance on the front surface of a fused silica is detected using, as the excitation light, evanescent light which is generated, from a laser beam incident from the rear surface of the fused silica, at an interface between the front surface of the fused silica and a solution layer. Generally, the intensity of evanescent light decays exponentially as the evanescent light travels further away from a refractive index interface plane, and decays to 1/e at a distance of around 150 nm from the refractive index interface plane. Accordingly, in the fluorescence detection using the evanescent light as the excitation light, an effect of the fluorescence emitted from a material other than the target substance to be detected, can be reduced significantly, and as a result, the fluorescence detection can be carried out with high contrast.

In P. N. A. S. 2003, Vol. 100, pp. 3960-3964 (Non-Patent Document 1), DNA elongation is detected using the above-described method. Specifically, first, a primer labeled with a Cy3 molecule is supplied onto a fused silica where a single DNA molecule is fixed by the protein binding of biotin-avidin. The positional information on the target DNA is recognized from the fluorescence intensity obtained by hybridization of the supplied primer and the target DNA molecule. Subsequently, DNA elongation of the primer molecule is performed, and then the DNA elongation is specifically detected from the positional information and the fluorescence generated from a dNTP molecule that is introduced in the DNA elongation.

In Anal. Chem. 2003, 75, pp. 6629-6633 (Non-Patent Document 2), more sensitive fluorescence-detection has been attempted using a plasmon resonance that is caused by introducing a silver thin film onto a fused silica. The plasmon resonance is a phenomenon of the resonance that is caused by the coupling of free electrons localized in a metal with an oscillating electric field of incident light. An enhanced electric field generated by the resonance causes enhanced excitation light and fluorescence, and as a result, highly sensitive fluorescence-detection can be expected. As such a metal that provides a strong resonance in a visible range, gold, silver, and the like are known.

On the other hand, in U.S. Pat. No. 6,917,726 (Patent Document 1), the fluorescence of a target substance is detected using a near-field light coming from an opening portion formed in an aluminum thin film expected to produce a light shielding effect, the opening portion sufficiently smaller than the wavelength of excitation light.

SUMMARY OF THE INVENTION

However, in the technique of Non-Patent Document 1, a complicated liquid-exchange process is required for the identification of the measurement position of a target substance, Moreover, the fluorescence emitted from a floating molecule present around the target substance acts as a noise. This noise leads to misrecognition of the measurement position of the target substance. Furthermore, if a fluorescent-labeled primer for identifying the measurement position is present around the target substance, such a measurement position would need to be excluded from the evaluation target. As a result, it would not be possible to measure a large number of different target substances at one time.

Similarly, also in the technique of Non-Patent Document 2, the noise from a floating molecule around a target substance is high.

On the other hand, in Patent Document 1, for the purpose reducing the noise, aluminium expected to produce a shielding effect is arranged on the fused silica except for the opening portion. However, since the reflectivity of the interface between the fused silica and the aluminium is not 100%, the noise due to leakage light from the aluminum thin film is generated. This noise becomes more eminent as the concentration of floating molecules increases.

An object of the present invention relates to detecting a target substance with high contrast.

The present invention relates to an analysis of a target substance using a light-transmitting substrate and a metal for inducing plasmon resonance, in which a low refractive index layer is provided. The low refractive index layer includes an opening portion therein, forms an interface with the substrate, and has a lower refractive index than the substrate. Light is emitted from a substrate side so as to be totally reflected at the interface, and to irradiate the metal arranged in the opening portion with evanescent light. Then, light that is generated from the target substance by plasmon resonance of the evanescent light is detected.

According to the present invention, the radiation of evanescent light to a material other than a target substance can be reduced, and light emission from the material other than the target substance, e.g., a molecule floating around the target substance, can be reduced.

DESCRIPTION OF THE PREFERRED EMBODIMENTS

Figure 1:
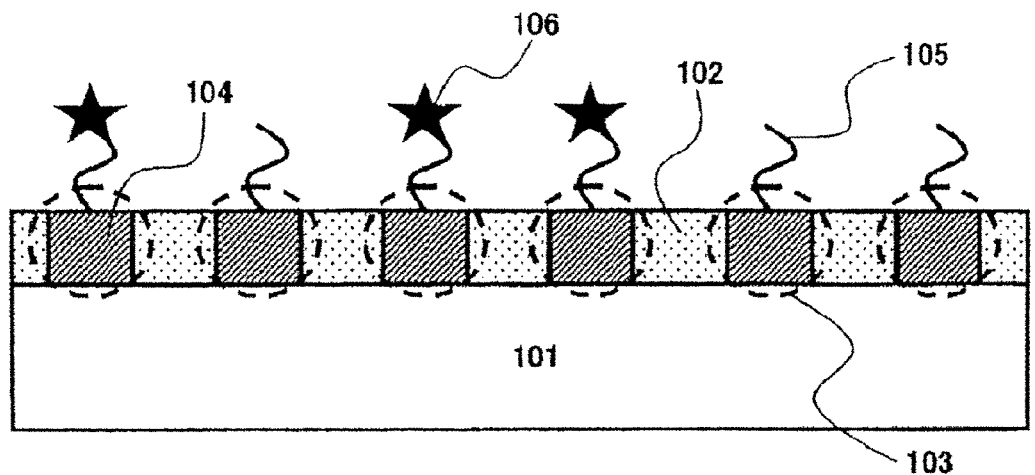
FIG. 1 is a view for illustrating an example of a device for detecting a target substance according to the present invention.
Figure 2:
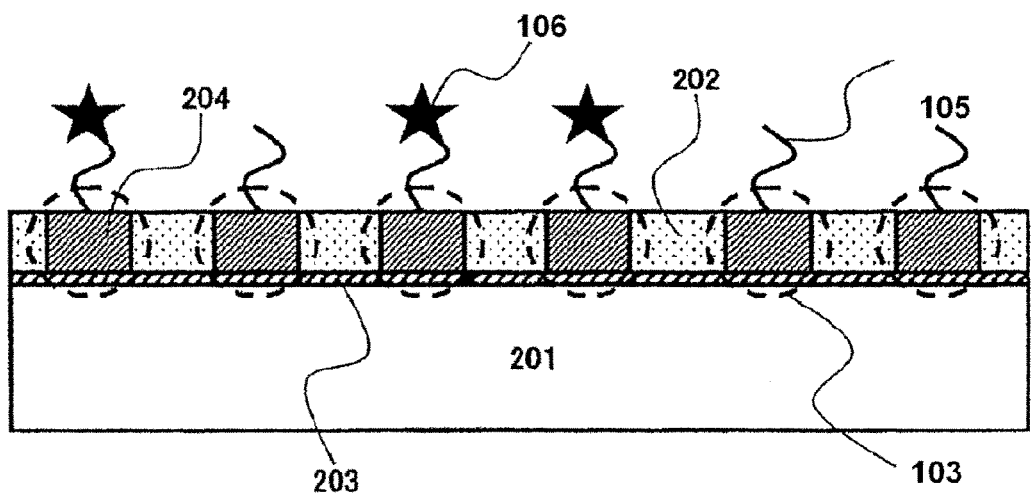
FIG. 2 is a view for illustrating an example of the device for detecting a target substance according to the present invention.

Hereinafter, the above-described and other innovative features and effects of the present invention will be described with reference to the accompanying drawings. Note that the drawings are merely used for the purpose of understanding the present invention, and do not limit the scope of the right of the present invention.

Embodiment 1

A preferred mode of a device according to this embodiment is described in detail with reference to FIG. 1.

The device of this embodiment is a device for simultaneously detecting a great number of target substances at one time. The device includes: a light-transmitting base member; and a low refractive index layer on the base member, the low refractive index layer composed of a material having a refractive index lower than the base member. A great number of opening portions are present in the low refractive index layer or low refractive layer and on the base member containing the layer. With the total internal reflection at the interface, on the base-member side, of the low refractive index layer, the leakage light from the low refractive index layer other than the area of the opening portions can be completely shielded, so that the light emission from a floating molecule but not the target substance can be reduced significantly.

Moreover, in the device of this embodiment, a metal capable of inducing plasmon resonance, or a structure composed of a plurality of materials including this metal is present inside the opening portion. Enhancement of the excitation light by the plasmon resonance can specifically increase only the light emission from the target substance.

Moreover, in the device of this embodiment, a high refractive index layer whose refractive index is higher than the material for forming the low refractive index layer is present on the low refractive index layer. Since the evanescent light generated from the total internal reflection can be reflected at an interface between the low refractive index layer and the high refractive index layer, noise generated from the low refractive index layer other than the area of the opening portions can be reduced more significantly.

Moreover, in the device of this embodiment, a probe for detecting a target substance is fixed onto the metal structure. By fixing a different probe for each metal structure, a great number of target substances can be detected simultaneously at one time.

Moreover, in the device of this embodiment, the maximum opening length of the opening portions is smaller than the wavelength of light used for detection. The detection using the near-field light from the opening portion can reduce a noise from a floating molecule but not the target substance, significantly.

Moreover, in the device of this embodiment, the opening portions are arrayed in the form of a grid. Since the distance between the target substances is uniform, a non-specific signal caused by a dust or the like can be ignored simply, and also the positional information on the target substance can be easily recognized. Accordingly, a great number of target molecules can be detected at one time with a high throughput.

Moreover, in a detection method according to this embodiment, light is totally reflected at the interface, on the base-member side, of the low refractive index layer of the device. The distance from the interface where the total internal reflection occurs, to an interface which a solution is in contact with makes it possible to reduce the light intensity of an evanescent wave significantly. Accordingly, the light emission from a floating molecule but not the target substance can be reduced significantly.

Moreover, in the detection method according to this embodiment, a fluorescent label is attached to a target substance for fluorescence detection. The fluorescence detection is a widely-used labeling method, so that existing detection methods can be generally used.

Moreover, a detection apparatus according to this embodiment includes: a means for holding a device; a reaction chamber, capable of exchanging solutions, on the device; and a means for irradiating the device with light; a means for detecting light from an opening portion. The apparatus including these components can continuously detect a solution containing a target substance with a high throughput.

The material used for a light-transmitting substrate 101, is not particularly limited as long as it is capable of transmitting light. Examples of such materials include one kind, or two or more kinds selected from the group consisting of plastic, inorganic polymer, metal, natural polymer, and ceramic. Specifically, the examples of plastic include polyethylene, polystyrene, polycarbonate, polypropylene, polyamide, a phenol resin, an epoxy resin, a polycarbodiimide resin, polyvinyl chloride, polyvinylidene fluoride, polyfluoroethylene, polyimide, an acrylic resin, and the like. The examples of inorganic polymer include glass, crystal, carbon, silica gel, and graphite. The examples of metal include solid metals at normal temperature, such as gold, platinum, silver, copper, iron, aluminium, magnet, and the like. The examples of ceramic include sapphire, alumina, silica, silicon carbide, silicon nitride, boron carbide, and the like. However, preferable are quartz, crystal, various kinds of optical glass, such as BK-7 and SF-2, sapphire, and the like, which are excellent in light transmission, have a high flatness of the base-member interface, and further tend to keep the flatness.

The material used for a low refractive index layer 102, which is a low refractive index layer for forming the interface between the substrate, which has a refractive index lower than the substrate and has an opening portion therein, is not particularly limited as long as it is a material having a smaller refractive index than a material constituting the base member. Examples of such a material includes: various kinds of oxides, such as silicon dioxide, alumina, gallium oxide, hafnium oxide, or magnesium oxide; and various kinds of fluorides, such as aluminum fluoride, calcium fluoride, cerium fluoride, lanthanum fluoride, lithium fluoride, magnesium fluoride, neodymium fluoride, samarium fluoride, or ytterbium fluoride. Moreover, the thickness of the low refractive index layer is also not particularly limited, however, it is more preferable to be at least capable of forming a uniform film with the thickness, and the thickness is desirably smaller than the wavelength of evanescent light generated from excitation light. More specifically, the thickness is preferably in the range of 5 nm to 1000 nm.

For a minute opening portion 103, i.e., an opening portion in which a metal for inducing plasmon resonance is arranged, as long as the opening length of the largest opening portion is smaller than the wavelength of light used for detection, both this length and shape thereof are not particularly limited.

A metal structure (or metal) 104 capable of inducing plasmon resonance is not particularly limited as long as it is composed of a material in which the plasmon is generated at an interface between a probe or a solution. Examples of such a metal structure (or metal) include: noble-metal elements, such as gold, silver, copper, and platinum; and an intermetallic compound or alloy composed of these elements. Moreover, although the size or shape thereof is not particularly limited, a size no greater than 1000 nm, which evanescent light or near-field light reach easily, is more preferable.

A probe 105 is not particularly limited as long as it interacts with a target substance 106. Examples of such a probe include a nucleic acid, a protein, a sugar chain, lipid, and a complex thereof. More specifically, DNA, RNA, an aptamer, a gene, a chromosome, a cell membrane, a virus, an antigen, an antibody, a lectin, a hapten, a receptor, an enzyme, a peptide, a shpingoglycol, a sphingolipid, and the like, can be enumerated.

The target substance 106 is not particularly limited as long as it interacts with the probe 105. Examples of such a target substance include: a nucleic acid, a protein, a sugar chain, lipid, a complex thereof, and a compound capable of constituting these molecules by a chemical reaction, an enzyme reaction, or the like. More specifically, deoxynucleotide-3-phosphate used in DNA synthesis, nucleotide-3-phosphate used in RNA synthesis, and the like, are enumerated. On the other hand, the fluorescence molecule used in labeling is also not particularly limited as long as it emits fluorescence.

As the detection device, in addition to the one shown in FIG. 1, those with structures shown in FIG. 2 to FIG. 5 can be used. A layer 203 of FIG. 2 improves an adhesive strength between a substrate 201 and a metal structure 204 and an adhesive strength between the substrate 201 and a low refractive index layer 202. Examples of a material of the layer include: chromium, tantalum, tungsten, vanadium, yttrium, cobalt, neodymium, titanium, nickel, and an alloy, nitride, or oxide thereof.

Figure 3:
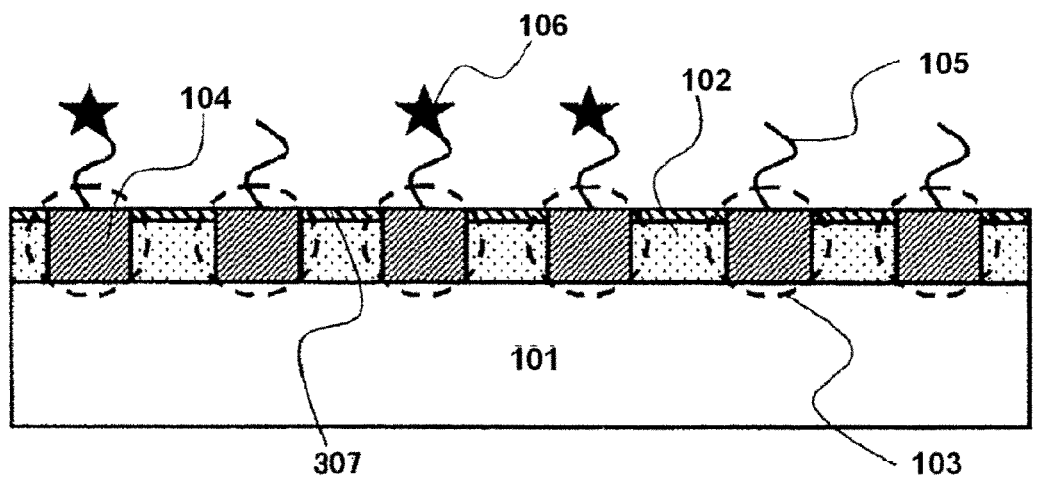
FIG. 3 is a view for illustrating an example of the device for detecting a target substance according to the present invention.
Figure 4:
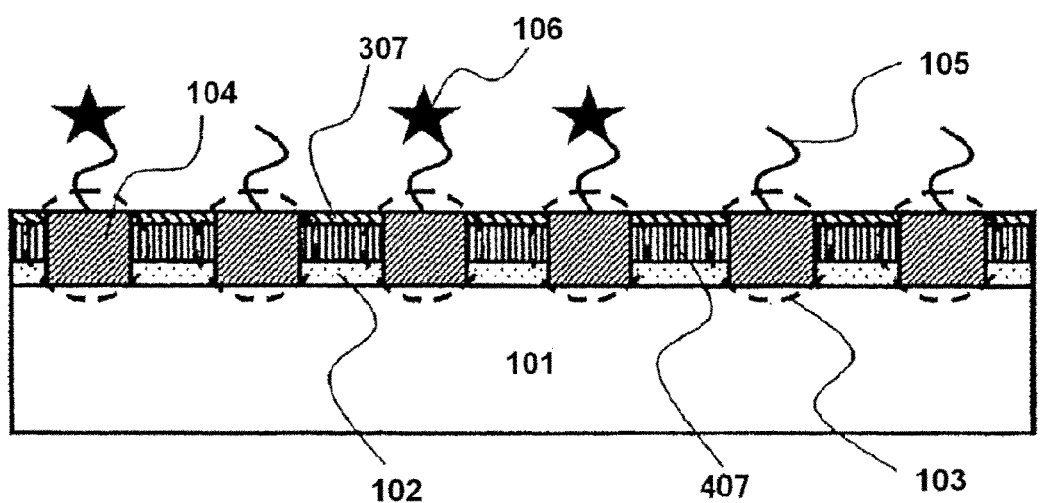
FIG. 4 is a view for illustrating an example of the device for detecting a target substance according to the present invention.

Reference numeral 307 of FIG. 3 represents a protective layer for the purpose of: the prevention of adsorption of non-specific materials other than a target substance; the prevention of dissolution of the low refractive index layer; or the corrosion prevention. Examples of a material of the protective layer include: inorganic compounds, such as a silicon dioxide and a silicon nitride, and organic compounds, such as a silane compound. Reference numeral 407 of FIG. 4 represents a layer for improving the shielding effect against evanescent light. For such layer, a material having a high refractive index and having a promising high adhesiveness to the low refractive index layer is generally preferable. Examples of such a material include: chromium, tantalum, tungsten, vanadium, yttrium, cobalt, neodymium, titanium, nickel, and an alloy, nitride, or oxide thereof.

Figure 5:
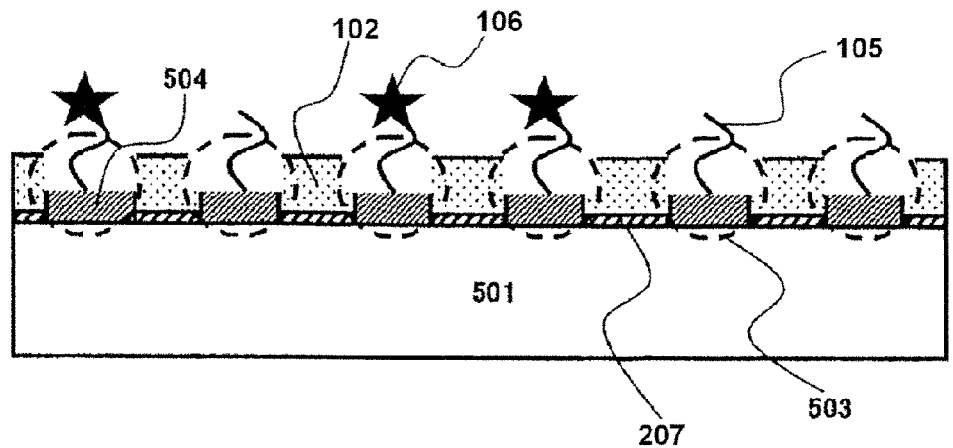
FIG. 5 is a view for illustrating an example of the device for detecting a target substance according to the present invention.

FIG. 5 shows an example, in which a metal structure 504 does not occupy whole interior of an opening portion 503. Generally, the light intensity of near-field light coming from an opening portion decays with the distance from the opening portion. Accordingly, in a detection device shown in FIG. 5, since the distance from the bottom surface of the opening portion to a probe is short, higher fluorescence intensity can be expected. Moreover, as a method for improving the enhancing effect due to plasmon resonance, there is a method of depositing a fine gold particle on the gold structure 504. Specifically, after the above-described device is annealed at 350° C. for 3 hours, a monolayer of aminoethanethiol deposited on the surface of the gold structure by self-assembly is dipped in a gold colloid suspension liquid to thereby deposit a gold nano particle.

Device

The preparation procedure of the device for detecting a target substance used in this embodiment is described with reference to FIG. 6. As a substrate 601, a 3-inch sapphire wafer having a thickness of 0.5 mm is used. On the substrate, an electron beam resist (ZEP520) 602 of a positive type is coated using a spin coater. Then, after a region of 1 mm square is exposed with an electron beam using an electron beam lithography system, development is performed to provide a large number of opening portions ((φ: 100 nm) 603 at 1 µm pitches. Furthermore, after gold (thickness 100 nm) is sputtered using a sputtering apparatus, a gold structure 604 is prepared using a lift-off process. Then, after silicon dioxide (thickness: 200 nm) is sputtered, the silicon dioxide is anisotropically etched with RIE (Reactive Ion Etching) using an SF6 gas to fabricate a device having a low refractive index layer 605. Finally, ultrasonic cleaning with acetone, isopropyl alcohol, and ultrapure water is performed to the obtained device. The obtained device is processed with a 6-amino-1-hexanethiol solution and a biotinylated succinimidester solution to introduce a probe (biotin) 606 on the surface of the gold structure 604.

Analyzer and Analysis Method

Moreover, an analyzer and an analysis method using the device are described with reference to FIG. 7.

A device 705 as described above is installed in a reaction chamber which is a chamber capable of holding a solution containing a target substance at the low refractive index layer side. The reaction chamber includes a cover plate 701, a detection window 702, an injection inlet 703 that is a solution exchanging port, and a discharge outlet 704. As the material of the cover plate 701 and the detection window 702, PDMS (Polydimethylsiloxane) is used. Moreover, the thickness of the detection window 702 is set to 0.17 mm.

Out of laser beams 709 and 710 oscillated from a YAG laser source (wavelength of 532 nm, output power of 20 mW) 707 and a YAG laser source (wavelength of 355 nm, output power of 20 mW) 708, which are light sources for irradiating light from the base member side, only the laser beam 709 is circularly polarized with a λ/4 plate 711. Then, the two laser beams are adjusted with a dichroic mirror 712 (light of no greater than 410 nm is reflected) so as to be coaxial with each other. Thereafter, the two laser beams are converged with a lens 713, and are then irradiated to the device 705 via a prism 714 at no less than the critical angle. A fluorescent substance present on the surface of the device 705 is excited with the laser radiation, and a part of the fluorescence is emitted through the detection window 702. In other words, the light is irradiated from the light sources so as to be totally reflected at an interface between the base member and the low refractive index layer, and so that the metal for inducing plasmon resonance may be irradiated with evanescent light.

Moreover, the fluorescence emitted from the detection window 702 is made to be a parallel beam by an objective lens 715 (×60, NA 1.35, operating distance of 0.15 mm), and the background light and excitation light are shut off by an optical filter 716, and the fluorescence is imaged on a two-dimensional CCD camera 718 by an imaging lens 717. In other words, light generated from the target substance by plasmon resonance of the evanescent light is detected by the detector.

Figure 8:
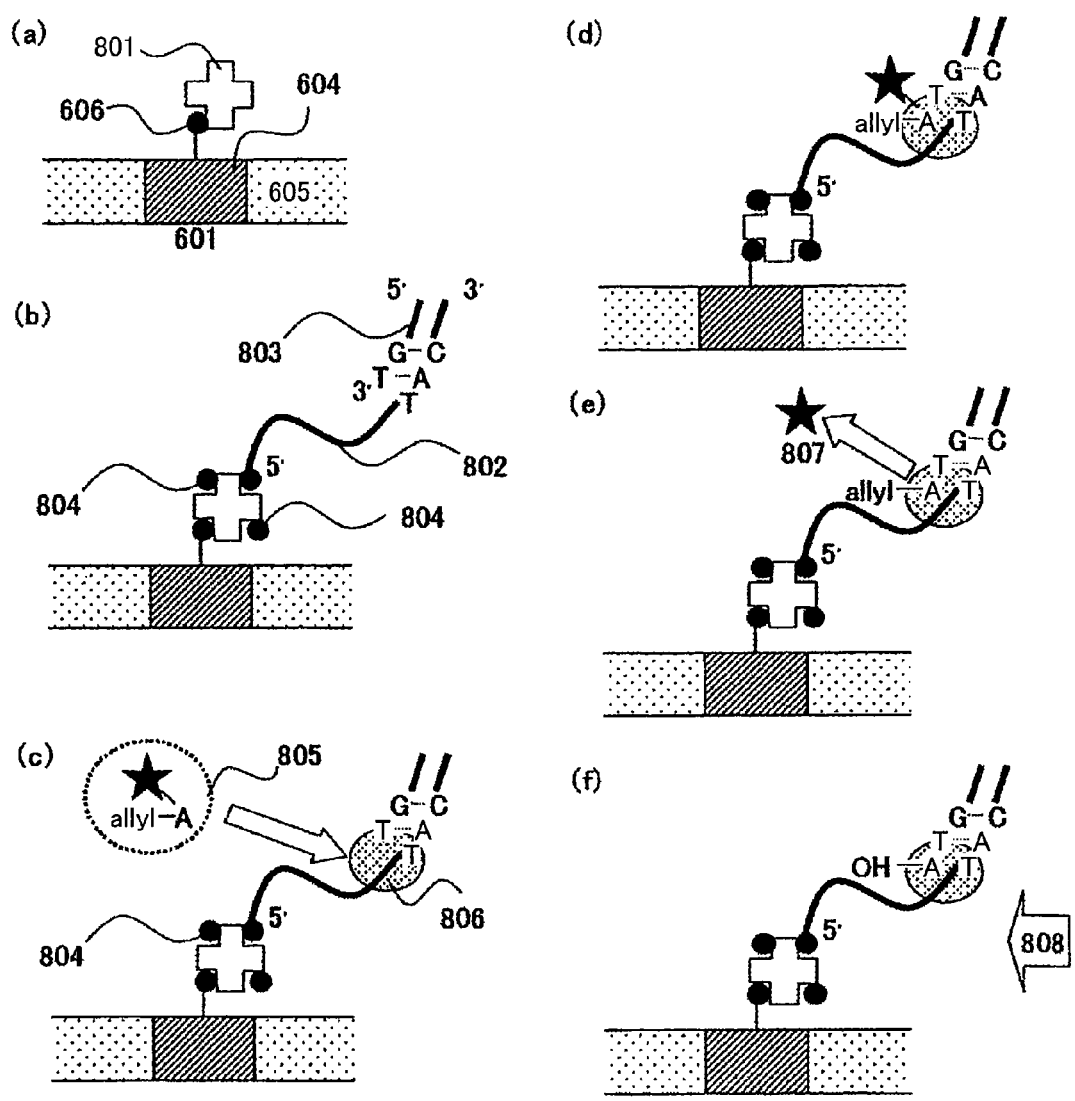
FIG. 8 is a view for illustrating a branching method shown in Embodiment 1 of the present invention.

Hereinafter, steps of a stepwise elongation reaction are described using FIG. 8. The reaction process is carried out in accordance with Non-Patent Document 1 and P. N. A. S. 2005, Vol. 102, pp. 5932-5937. A buffer added with streptavidin is introduced into a reaction chamber 706 from the injection inlet 703, and streptavidin 801 is bound to biotin 606 on the gold structure 604 of the device 705 to form a biotin-avidin complex (FIG. 8A). A primer 803 is hybridized to a single-stranded template DNA 802 that is a biotin-modified target. Then, a buffer added with the template DNA-primer complex and a large excess of biotin 804 is introduced into the injection inlet 703 where the template DNA-primer complex of a single molecule is fixed via biotin-avidin binding (FIG. 8B). After the fixing reaction, the redundant template DNA-primer complex and biotin are washed away with a wash buffer. Next, Thermo Sequenase Reaction buffer, which is added with Thermo Sequenase polymerase 806 and dATP (3'-O-allyl-dATP-PC-R6G) 805 whose 3' terminal labeled with a fluorescent substance R6G is modified with an allyl group, is introduced from the injection inlet 703 to the reaction chamber 706 to carry out the elongation reaction. At this time, suppose a case where the base on the sequence of the single-stranded template DNA 802, which is present on a complementary position of a position next to the base at the 3' terminal of the primer 803, is T. In this case, the dATP 805 is incorporated into the template DNA-primer complex by a polymerase elongation reaction. Moreover, since the 3' terminal of the dATP 805 is modified with an allyl group, one base or more will not be incorporated into the template DNA-primer complex. After the elongation reaction, the unreacted dATP 805 and a polymerase 806 are washed away from the reaction chamber 706 using a wash buffer. Then, the laser beam 709 oscillated from the YAG laser source 707 is irradiated to the chip to carry out fluorescence detection (FIG. 8D). Then, it is determined whether or not the dATP has been incorporated into the template DNA-primer complex on the basis of the presence or absence of fluorescence at a predetermined position. Next, the laser beam 710 oscillated from the YAG laser source 708 is irradiated to the chip to remove the fluorescent substance 807 labeled to the dATP 805 which is incorporated into the complex, by photo cutting (FIG. 8E). Next, a solution 808 containing palladium is introduced to the interior of the reaction chamber 706 to exchange the allyl group at the 3' terminal of the dATP which is incorporated into the complex, with a hydroxyl group by palladium catalyst reaction (FIG. 8F). The exchange of the allyl group at the 3' terminal into the hydroxyl group makes it possible to resume the elongation reaction of the template DNA-primer complex. After the catalytic reaction, the reaction chamber 706 is washed using a wash buffer. By repeating the process from FIG. 8C to the above-described washing with respect to each dNTP, i.e., A→C→G→T→A→, the sequence of the fixed single-stranded template DNA 802 is determined. In this system, since the fluorescence from a plurality of the gold structures 604 can be simultaneously measured, the base types of dNTP that is incorporated into a plurality of different template DNA-primer complexes, i.e., the sequence of a plurality of template DNAs, can be determined simultaneously. Moreover, when the device of this embodiment is used, only the fluorescence from a target substance generated by the enhanced excitation light due to plasmon resonance by gold can be increased specifically, and at the same time, the noise generated from a fluorescence molecule that is non-specifically adsorbed on the low refractive index layer 605 can be reduced. From the above, according to this embodiment, a large number of target substances can be detected at one time with high contrast.

Embodiment 2

Figure 9:
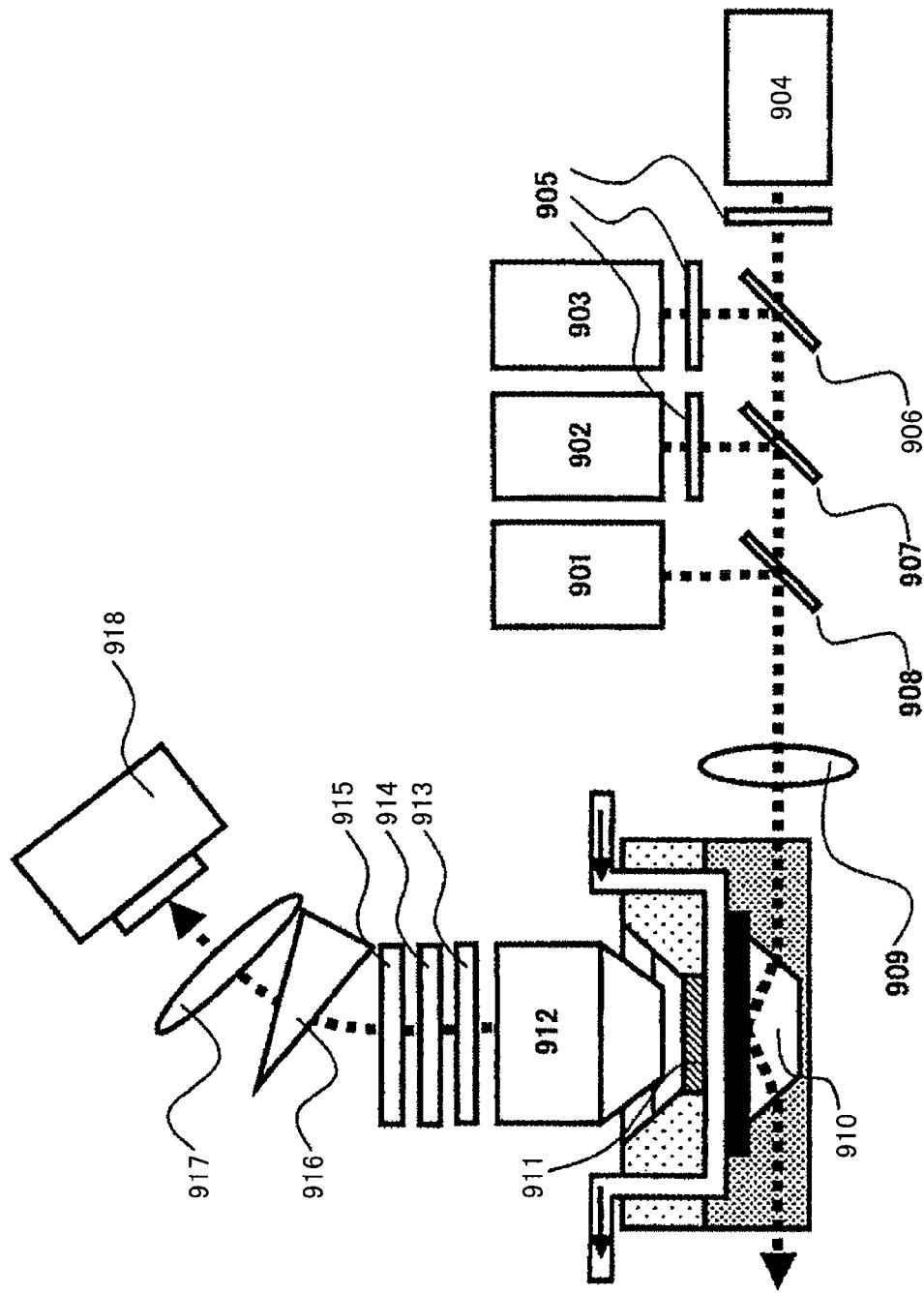
FIG. 9 is a view for illustrating an analyzer shown in Embodiment 2 of the present invention.

FIG. 9 shows a second embodiment. In this embodiment, DNA sequencing based on a stepwise elongation reaction using four kinds of fluorescent substances is carried out. Hereinafter, main differences from Embodiment 1 are described.

Figure 6:
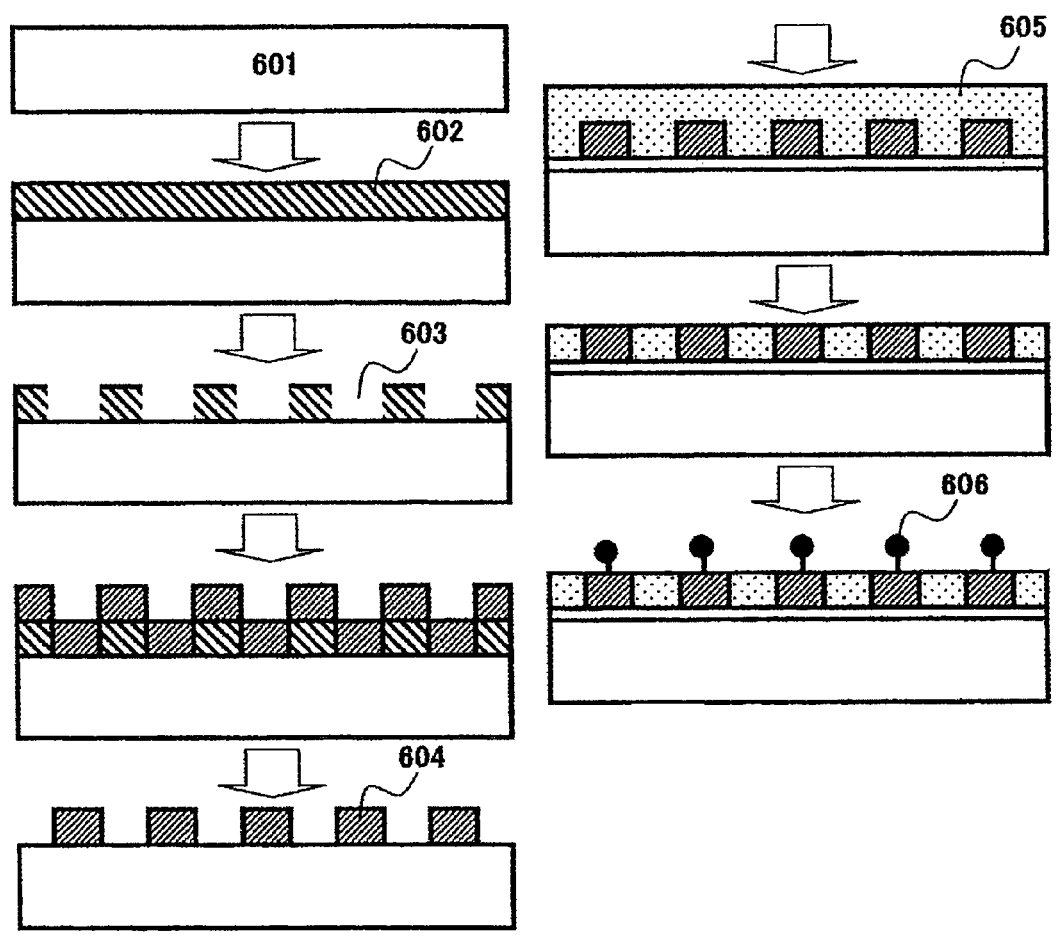
FIG. 6 is a view for illustrating a method for manufacturing a device shown in Example 1 of the present invention.
Figure 7:
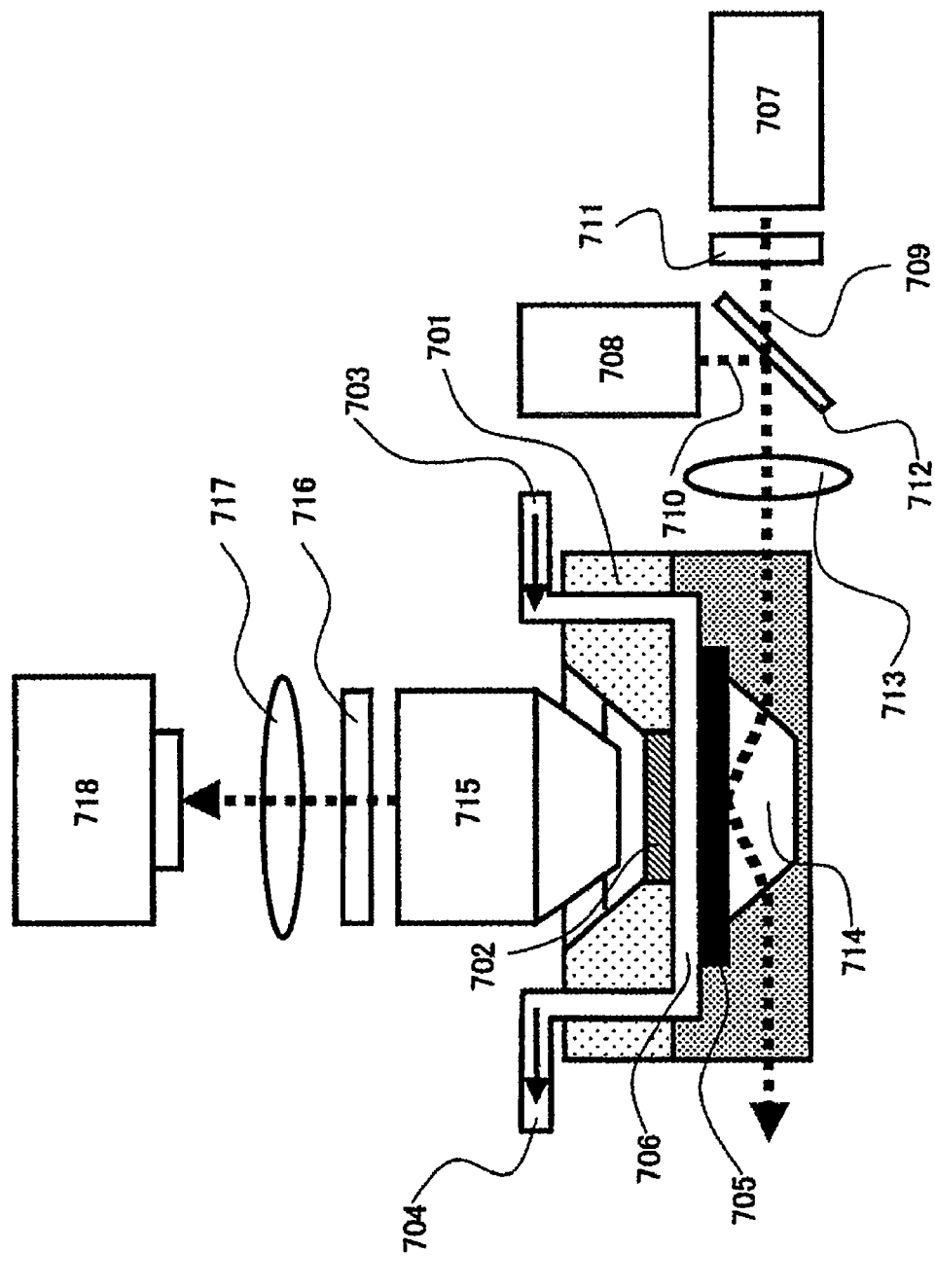
FIG. 7 is a view for illustrating an analyzer shown in Embodiment 1 of the present invention.

The configuration of the chip is equivalent to that of FIG. 6, and the configuration of the chamber portion is equivalent to that of FIG. 7.

For the laser beam oscillated from each of a YAG laser source (wavelength of 355 nm, output power of 20 mW) 901, an Ar-ion laser source (wavelength of 488 nm, output power of 20 mW) 902, a YAG laser source (wavelength of 532 nm, output power of 20 mW) 903, and a He—Ne laser source (wavelength of 594 nm, output power of 20 mW) 904, the laser beams other than the laser beam from the YAG laser source 901 are circularly polarized with $\lambda/4$ plates 905, and then the laser beams are adjusted with dichroic mirrors 906 (light of no greater than 555 nm is reflected), 907 (light of no greater than 520 nm is reflected), and 908 (light of no greater than 410 nm is reflected) so that the optical axes of all the laser beams may be coaxial with each other. Then, all the laser beams are converged with a lens 909, and enter the chip from underneath thereof through a prism 910 at no less than the critical angle.

The fluorescence obtained by the laser radiation is emitted through a detection window 911 to the outside of the chamber portion. Then, the emitted fluorescence is made to be a parallel beam by an objective lens 912 (×60, NA 1.35, operating distance of 0.15 mm). Subsequently, the unwanted excitation light and background light are shut off by a band pass filter 913 (which transmits light of 520 nm to 650 nm), a notch filter 914 (a cut-off center wavelength is 532 nm, a half-value width is 14 nm), and a notch filter 915 (a cut-off center wavelength of 594 nm, a half-value width 22 nm). Thereafter, after the wavelength is dispersed by a prism 916, the resultant fluorescence is imaged on a two-dimensional CCD camera 918 by an imaging lens 917.

Steps of the stepwise elongation reaction are basically the same as those of Embodiment 1 except that the elongation reaction is carried out at one time using four kinds of dNTPs (3'-O-allyl-dGTP-PC-Bodipy-FL-510, 3'-O-allyl-dTTP-PC-R6G, 3'-O-allyl-dATP-PC-ROX, and 3'-O-allyl-dCTP-PC-Bodipy-650) whose 3' terminals labeled with four different kinds of fluorescent substances, respectively, are each modified with an allyl group. At this time, as in Embodiment 1, the base type of the dNTP can be identified by identifying the fluorescence wavelength of the fluorescent substance labeled to the dNTP that is incorporated into the template DNA-primer complex. Note that, in Embodiment 1, in order to determine one base of a plurality of template DNAs, a series of sequences, i.e., "introduce dNTP and a polymerase into a channel→elongation reaction→washing→fluorescence measurement→fluorescence cutting→hydroxylization of 3' terminal→washing", needs to be carried out on four kinds of dNTPs; in other words, the series of sequences needs to be carried out four times. With the use of spectral elements within a detection unit as in the present system, the elongation reaction can be carried out while four kinds of dNTPs flow into a reaction chamber simultaneously. Therefore, the number of times of the series of sequences required to determine one base of a plurality of template DNAs may be one. For this reason, the time consumed for the DNA sequencing in this embodiment can be reduced by about ¼ as compared with that of Embodiment 1.

Embodiment 3

In this embodiment, DNA sequencing based on a continuous elongation reaction is carried out. The continuous elongation reaction refers to a reaction method in which the elongation reaction is carried out continuously without liquid exchange after the elongation of one base. Hereinafter, main differences from Embodiment 1 are described. For the continuous elongation reaction, see P. N. A. S. 2008, Vol. 105, pp. 1176-1181 incorporated herein by reference.

For the configuration of the chip, the following processings are carried out without introducing the probe (biotin) 606. First, the device is dipped in a methanol solution of 3% aminopropyltrimethoxysilane for 5 minutes, and is then baked at 180° C. for 2 hours to introduce an amino group onto $SiO_2$. Furthermore, the substrate is dipped in a PEG-NHS ester disulfide solution (pH 8.0, 100 mM tetraethylammonium hydroxide) of 4 mM for one hour to introduce a blocking layer of PEG onto $SiO_2$. Then, the substrate is dipped in an ethanol solution of 11-amino-1-undecanethiol of 10 mM to introduce an amino group onto the gold surface. On the other hand, the configuration of the chamber portion is equivalent to that of FIG. 7.

Hereinafter, steps of the continuous elongation reaction are described. After DNA which is hybridized with a primer is mixed into a DNA polymerase, the solution is ice-cooled. The solution is introduced from the injection inlet 703 to the reaction chamber 706 to adsorb the complex of DNA polymerase and DNA onto the aminated gold surface. After the adsorption, the redundant complex of DNA polymerase and DNA is washed away with a wash buffer. Next, a solution containing dATP, dGTP, dCTP, and dTTP labeled with a fluorescent substance R6G is introduced into the reaction chamber 706. Then, the reaction chamber 706 is brought to room temperature to start the elongation reaction. The fluorescence molecule of dATP that is introduced in the elongation reaction and labeled with R6G is measured. In this embodiment, only dATP is fluorescence measured; however, the labeling of dATP, dGTP, dCTP, and dTTP with different dyes and the fluorescence measurement thereof enable determination of the base sequence without liquid exchange. According to the analyzer of the present invention, a fluorescence molecule, which is a target substance, can be measured with high contrast because the light emission originating from a floating unreacted substance can be reduced.

What is claimed is:

1. an apparatus for analyzing a target substance, comprising:
    a continuous plate-shaped light-transmitting substrate having a flat surface;
    metal structure components and low refractive index layers disposed on the flat surface of the substrate, the metal structure components and the low refractive index layers being disposed alternately, in a grid-like manner at regular intervals so that an adjacent metal structure component and a low refractive index layer are disposed in contact with each other and the metal structure components are separated from each other and the low refractive index layers are separated from each other;
    a chamber configured to hold a solution containing a target substance at a low refractive index layer side;
    a light source which emits light toward the substrate so as to totally reflect the light at an interface between the low refractive layers and the substrate, and irradiate the metal structure components with evanescent light; and
    a detector which detects light generated from the target substance by plasmon resonance of the evanescent light, wherein:
    a different single molecule probe is fixed onto each metal structure, and a protective layer is provided on the low refractive index layers, and
    a distance from the flat surface of the substrate to an upper surface of the metal structures is smaller than a distance from the flat surface of the substrate to an upper surface of the low refractive index layers.

2. The apparatus according to claim 1, wherein the metal structure components comprise a plurality of materials.

3. The apparatus according to claim 1, further comprising a high refractive index layer on the low refractive index layers, wherein
    the high refractive index layer has a refractive index higher than a material for forming the low refractive index layer.

4. The apparatus according to claim 1, wherein the maximum length of the metal structure components is smaller than a wavelength of light used for detection.

5. The apparatus according to claim 1, wherein
    a fluorescent label is attached to the target substance, and
    the target substance is fluorescence-detected.

6. A method for analyzing a target substance, comprising the steps of:
    preparing a detection device including: a continuous plate-shaped light-transmitting substrate having a flat surface; metal structure components and low refractive index layers disposed on the flat surface of the substrate, the metal structure components and the low refractive index layers are disposed alternately, in a grid-like manner at regular intervals so that an adjacent metal structure component and a low refractive index layer are disposed in contact with each other and the metal structure components are separated from each other and the low refractive index layers are separated from each other;
    holding a liquid containing a target substance onto the detection device;
    emitting light towards the substrate so as to totally reflect the light at an interface between the low refractive index layers and the substrate, and irradiate the metal structures with evanescent light; and
    detecting light that is generated from the target substance by plasmon resonance of the evanescent light,
    wherein:
    a different single molecule probe is fixed onto each metal structure, and a protective layer is provided on the low refractive index layers, and
    a distance from the flat surface of the substrate to an upper surface of the metal structures is smaller than a distance from the flat surface of the substrate to an upper surface of the low refractive index layers.

7. The method according to claim 6, wherein the metal structure components comprise a plurality of materials.

8. The method according to claim 6, wherein
    a high refractive index layer is present on the low refractive index layer, and
    the high refractive index layer has a refractive index higher than a material for forming the low refractive index layer.

9. The method according to claim 6, wherein the maximum length of the metal structure components is smaller than a wavelength of light used for detection.

10. The method according to claim 6, wherein
    a fluorescent label is attached to the target substance, and
    the target substance is fluorescence-detected.

* * * * *